United States Patent [19]

Woolard

[11] Patent Number: 4,867,782
[45] Date of Patent: Sep. 19, 1989

[54] NOVEL HERBICIDAL 2-SULFONYLIMINOTHIAZOLIDINES

[75] Inventor: Frank X. Woolard, Richmond, Calif.

[73] Assignee: ICI Americas Inc., Wilmington, Del.

[21] Appl. No.: 214,347

[22] Filed: Jul. 1, 1988

[51] Int. Cl.[4] .................... C07D 277/18; A01N 43/78
[52] U.S. Cl. .......................................... 71/90; 548/197
[58] Field of Search .............................. 548/197; 71/90

[56] References Cited

U.S. PATENT DOCUMENTS

| | | | |
|---|---|---|---|
| 3,671,537 | 6/1972 | Toldy et al. | 548/190 |
| 3,804,848 | 4/1974 | Behner et al. | 548/190 |
| 4,665,083 | 5/1987 | Lempert et al. | 548/190 |

FOREIGN PATENT DOCUMENTS

| | | | |
|---|---|---|---|
| 446994 | 3/1948 | Canada | 548/197 |
| 265162 | 4/1988 | European Pat. Off. | 548/190 |
| 4318776 | 8/1968 | Japan | 548/190 |

OTHER PUBLICATIONS

Dains, et al., JACS 44, 2637–2643 (1922).
Abdullaev et al., CA 91: 151104S (1979).

Primary Examiner—Robert Gerstl
Attorney, Agent, or Firm—Joel G. Ackerman

[57] ABSTRACT

Compounds having the formula

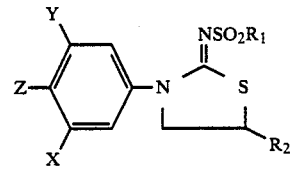

in which $R_1$ is $C_1$–$C_6$ alkyl; $C_1$–$C_6$ alkoalkyl; $C_2$–$C_6$ alkenyl; mono- or di- ($C_1$–$C_4$)alkylamino; phenyl; benzyl; or para-substituted phenyl or benzyl in which the substituent is halogen, cyano, nitro, $C_1$–$C_4$ alkyl, $C_1$–$C_4$ alkoxy, $C_1$–$C_4$ alkylthio or trifluoromethyl; $R_2$ is hydrogen, methyl, ethyl or chloromethyl; X is hydrogen, halogen, nitro, cyano, perhalomethyl, difluoro-methyl, pentafluoroethyl, $C_1$–$C_4$ alkyl, $C_1$–$C_4$ alkoxy, trifluoromethylthio, difluoromethoxy, trifluoromethoxy, tetrafluoroethoxy, methylsulfonyl, trifluoromethylsulfonyl, phenoxy, pyridyloxy, halo-substituted-phenoxy or -pyridyloxy, trifluoromethyl-substituted-phenoxy or -pyridyloxy, $C_1$–$C_4$ alkyloximinomethyl, benzyloximinomethyl, 1-($C_1$–$C_4$ alkyl)oximinoethyl and 1-benzyloximinoethyl; Y is hydrogen, halogen, nitro, cyano, perhalomethyl, difluoromethyl, pentafluoroethyl, $C_1$–$C_4$ alkyl, $C_1$–$C_4$ alkoxy, trifluoromethylthio, trifluoromethoxy, tetrafluoroethoxy, methylsulfonyl and trifluoromethylsulfonyl; and Z is hydrogen or fluoro if Y is hydrogen, or hydrogen if Y is other than hydrogen are useful as herbicides.

27 Claims, No Drawings

NOVEL HERBICIDAL 2-SULFONYLIMINOTHIAZOLIDINES

The present invention relates to certain-2-sulfonyliminothiazolidine herbicide compounds, compositions, process of preparation and method of use.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have the formula:

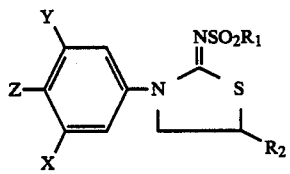

in which $R_1$ is $C_1$–$C_6$ alkyl; $C_1$–$C_6$ haloalkyl; $C_2$–$C_6$ alkenyl; mono- or di-($C_1$–$C_4$)alkylamino; phenyl; benzyl; or para-substituted phenyl or benzyl in which the substituent is halogen, cyano, nitro, $C_1$–$C_4$ alkyl, $C_1$–$C_4$ alkoxy, $C_1$–$C_4$ alkylthio or trifluoromethyl;

$R_2$ is hydrogen, methyl, ethyl or chloromethyl;

X is hydrogen, halogen, nitro, cyano, perhalomethyl, difluoromethyl, pentafluoroethyl, $C_1$–$C_4$ alkyl, $C_1$–$C_4$ alkloxy, trifluoromethylthio, difluoromethoxy, trifluoromethoxy, tetrafluoroethoxy, methylsulfonyl, trifluoromethylsulfonyl, phenoxy, pyridyloxy, halo-substituted-phenoxy or -pyridyloxy, trifluoromethyl-substituted-phenoxy or -pyridyloxy, $C_1$–$C_4$ alkyloxyiminomethyl, benzyloxyiminomethyl, 1-($C_1$–$C_4$ alkyl)oximinoethyl and 1-benzyloximinoethyl;

Y is hydrogen, halogen, nitro, cyano, perhalomethyl, difluoromethyl, pentafluoroethyl, $C_1$–$C_4$ alkyl, $C_1$–$C_4$ alkoxy, trifluoromethylthio, trifluoromethoxy, tetrafluoroethoxy, methylsulfonyl and trifluoromethylsulfonyl; and Z is hydrogen or fluoro if Y is hydrogen, or hydrogen if Y is other than hydrogen.

The compounds of this invention have been found to be active herbicides, possessing pre and/or post-emergence herbicidal activity against various types of weeds including broadleaf and grassy weeds. As mentioned below, some of the compounds demonstrate good control of weeds in certain crops such as cotton, wheat and rice.

Therefore this invention also relates to a method for controlling undesirable vegetation, in general comprising applying to a locus where control of such vegetation is desired, either prior or subsequent to the emergence of such vegetation, a herbicidally effective amount of a compound as described herein. In another aspect, the invention also relates to herbicidal compositions comprising an herbicidally effective amount of a compound as described herein, together with an inert diluent or carrier suitable for use with herbicides.

These compounds can be prepared by reacting a 2-iminothiazolidine of the formula

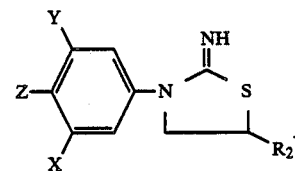

in which X, Y, Z and $R_2$ are as described above with an alkyl or arylsulfonyl halide of the formula Hal-$SO_2R_1$ in which Hal stands for halogen, preferably chloro or bromo, dissolved in an organic solvent and in the presence of a base, at a temperature of from about 0° C. to about 40° C., preferably from about 0° C. to about 30° C., most preferably from about 5° to about 10° C. The reaction is exothermic and is normally carried out at atmospheric pressure.

Suitable bases for use in this reaction include amines such as pyridine or, preferably, triethylamine. Other suitable bases will be apparent to those skilled in the art.

The reaction should be conducted in an organic solvent such as methylene chloride toluene, or benzene.

The starting 2-iminothiazolidines may be prepared according to any of several methods as convenient. For instance, U.S. Pat. No. 4,565,083 discloses several methods for production of compounds of this general type, including cyclization of an isothiocyanate and reaction of an iminothiazolidine with a substituted phenyl fluoride. According to another process, as described in Application Ser. No. 214,347 of Frank H. Woolard and Charles Kezerian, entitled "Process for Production of 2-Iminothiazolidines and Oxazolidines," filed concurrently herewith, these intermediates can be prepared by reacting an appropriately substituted phenyl cyanamide in a suitable solvent (for instance toluene or methyl ethyl ketone) with an episulfide and a base according to the reaction

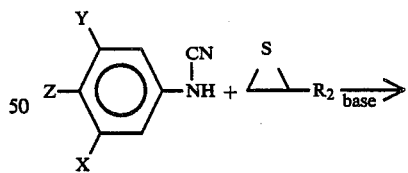

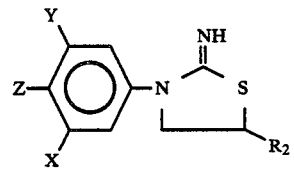

The starting phenyl cyanamides can be made by a number of different methods. These compounds are known in the literature. See, for example, *Organic Synthesis*, Vol. IV, p. 172 and German Patent Application (OLS) 3,538,128.

The example which follow illustrate production of compounds of this procedure.

EXAMPLE 1

Preparation of 2-Trifluoromethanesulfonylimino-3-(3-trifluoromethyl)phenyl-5-ethylthiazolidine (Compound 5 herein)

To a flask equipped with a stirrer, external ice bath, thermometer and pressure equalizing addition funnel carrying a nitrogen bubbler was added 2.50 g (9.1 mmol) of 2-imino-3-(3-trifluoromethyl)phenyl-5-ethyliminothiazolidine, 1.27 ml (9.1 mmol) of triethylamine and 30 ml of benzene. The mixture was stirred, cooled to 10° C. and the addition funnel charged with 0.97 ml (9.1 mmol) trifluoromethanesulfonyl chloride in 10 ml of benzene. The sulfonyl chloride solution was then added to the reaction mixture at such a rate that the temperature of the mixture did not rise above 15° C. (5 minutes). When the addition was completed, a gas chromatography trace showed some starting material left. An additional quantity of trifluoromethanesulfonyl chloride/triethylamine was then added until the starting material substantially disappeared. The semi-solid reaction mixture was washed in 2×50 ml portions of water, 1×50 ml of 3% HCl, 1×50 ml of brine, dried (over MgSO$_4$) and the solvent removed in vacuo to give 3.27 grams (g) (88%) of product as a yellow syrup. It was identified as the subject compound by spectroscopic techniques.

EXAMPLE 2

Preparation of 2-Chloromethanesulfonylimino-3-(3-cyano)phenyl-5-ethylthiazolidine (Compound 9 herein)

To a flask equipped with a stirrer, external ice bath, thermometer and pressure equalizing addition funnel was added 1.75 g (7.6 mmol) 2-imino-3-(3-cyano)phenyl-5-ethylthiazolidine, 25 ml of benzene and 0.84 g (8.0 mmol) triethylamine. The flask was immersed in the ice bath and the stirring contents cooled to 15° C. The addition funnel was charged with 1.13 g (7.6 mmol) of chloromethanesulfonyl chloride dissolved in 10 ml of benzene. The chloromethanesulfonyl chloride solution was then added drop-wise to the reaction mixture over a 10-minute period. When the addition was complete, gas chromatography indicated the reaction was complete. The semisolid reaction mixture was washed with 2×30 ml portions of water, 1×30 ml of 3% HCl, dried (over MgSO$_4$) and the solvent removed in vacuo to give 2.37 g (100%) of product as a caramel colored syrup. This was identified as the subject compound by spectroscopic techniques.

EXAMPLE 3

Preparation of 2-Chloromethanesulfonylimino-3-(3-trifluoromethyl-4-fluoro)phenyl-5-ethylthiazolidine (Compound 8 herein)

To a flask equipped with a stirrer, external ice bath, thermometer, and pressure equalizing addition funnel was added 2.50 g (8.6 mmol) of 2-imino-3-(3-trifluoromethyl-4-fluoro)phenyl-5-ethylthiazolidine, 25 ml of benzene and 1.28 g (8.6 mmol) triethylamine. The flask was immersed in the water bath and cooled to 15° C. The addition funnel was charged with 1.28 g (8.6 mmol) chloromethanesulfonyl chloride in 10 ml of benzene. This was added dropwise to the reaction mixture over a 10 minute period. When the addition was complete, gas chromatography indicated the reaction was done. The semi-solid reaction mixture was washed with 2×30 ml portions of water, 1×30 ml of 3% HCl, dried (over MgSO$_4$), and the solvent removed in vacuo to give a yellow syrup. The crude product was passed through a short column of silica gel with 70:30 hexanes/ethyl acetate as eluent to remove some polymeric material. Removal of the solvent in vacuo to gave 3.77 g (73%) of product as a yellow syrup. It was identified as the subject compound by spectroscopic analytical techniques.

Table I depicts representative compounds of this invention.

TABLE I

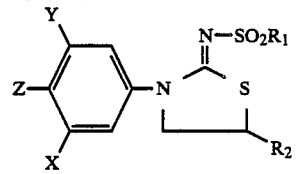

| Cmpd. No. | X | Y | Z | R$_1$ | R$_2$ | Physical Constant |
|---|---|---|---|---|---|---|
| 1 | CF$_3$ | H | H | 4-F—C$_6$H$_4$ | C$_2$H$_5$ | m.p. 124 |
| 2 | CF$_3$ | H | H | 4-Cl—C$_6$H$_4$ | C$_2$H$_5$ | m.p. 98.0–104.0 |
| 3 | CF$_3$ | H | H | CH$_3$ | C$_2$H$_5$ | thick syrup |
| 4 | CF$_3$ | H | H | CH$_2$Cl | C$_2$H$_5$ | thick syrup |
| 5 | CF$_3$ | H | H | CF$_3$ | C$_2$H$_5$ | waxy solid |
| 6 | CF$_3$ | H | H | vinyl | C$_2$H$_5$ | waxy solid |
| 7 | CF$_3$ | H | H | n-C$_4$H$_9$ | C$_2$H$_5$ | nD 1.5301 |
| 8 | Cl | H | F | CH$_2$Cl | C$_2$H$_5$ | thick syrup |
| 9 | CN | H | H | CH$_2$Cl | C$_2$H$_5$ | thick syrup |
| 10 | CF$_3$ | H | F | CH$_2$Cl | C$_2$H$_5$ | thick syrup |
| 11 | Cl | H | H | CH$_2$Cl | C$_2$H$_5$ | thick syrup |
| 12 | CF$_3$ | H | H | 4-CH$_3$—C$_6$H$_4$ | C$_2$H$_5$ | m.p. 103.0–108.5 |
| 13 | NO$_2$ | H | H | CH$_2$Cl | C$_2$H$_5$ | waxy solid |
| 14 | CF$_3$ | H | H | N(CH$_3$)$_2$ | C$_2$H$_5$ | thick syrup |
| 15 | CF$_3$ | H | H | C$_2$H$_5$ | C$_2$H$_5$ | waxy solid |
| 16 | CF$_3$ | H | H | n-C$_3$H$_7$ | C$_2$H$_5$ | thick syrup |
| 17 | CF$_3$ | H | H | CH$_2$CH$_2$CH$_2$Cl | C$_2$H$_5$ | nD 1.5365 |
| 18 | CF$_3$ | H | H | C$_6$H$_5$CH$_2$— | C$_2$H$_5$ | thick syrup |
| 19 | CF$_3$ | H | H | C$_6$H$_5$ | C$_2$H$_5$ | m.p. 94.0–99.0 |
| 20 | CF$_3$ | H | H | CH$_3$ | CH$_3$ | thick syrup |

Herbicidal Activity Tests

The compounds in Table I were tested for herbicidal activity as follows:

The herbicidal effect is observed by comparing the extent of weed control in test flats treated with the compounds against that occurring in similar control flats. All compounds were applied at 4.0 lb/A (4.48 kg/ha) to pre-emergence and post-emergence screening flats. An 80 gal/A (748.3 l/HA)spray volume is utlized. Post-emergence flats were seeded 12 days prior to treatment; pre-emergence flats one day prior to treatment. Overhead watering of pre-emergence flats and soil surface watering of post-emergence flats, so as to avoid wetting the foliage, was carried out for the duration of the test.

Weed seeds were planted in a flat at a seed depth of 0.5 inch (1.3 cm). Soil for flats was prepared using Keeton sandy loam soil fortified with 17-17-17 fertilizer (N—P$_2$O$_5$—K$_2$O on a weight basis) and Captan 80W. The test weeds were as follows:

| COMMON NAME | SCIENTIFIC NAME | ABR |
|---|---|---|
| Broadleaf Weeds: | | |
| annual morningglory | Ipomoea purpurea | AMG |
| velvetleaf | Abutilon theophrasti | VL |
| mustard | Brassica sp. | MD |
| Grasses: | | |

-continued

| COMMON NAME | SCIENTIFIC NAME | ABR |
|---|---|---|
| yellow nutsedge | *Cyperus esculentus* | YNS |
| foxtail | *Setaria sp.* | FT |
| watergrass | *Echinochloa crusgalli* | WG |
| wild oat | *Avena fatua* | WO |

The spray solutions were prepared by dissolving 240 mg of test compound in 20 ml of acetone containing 1% polyoxy ethylene sorbitan monolaurate emulsifier, then adding 20 ml of water to the resulting solution. The stock solutions were applied using a linear spray table. Pre-emergence flats are raised to the level of the post-emergence foliage canopy by setting the flats on a wooden block.

In both instances, either pre- or post-emergent testing, approximately 18 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in the Table below.

quent evaluations involving, for example, different weeds, lower application rates, varying application procedures, and/or selectivity with respect to crops. The weeds employed in these tests included those utilized in the tests just described, as well as a number of others such as one or more species of ryegrass (Lolium), Sorghum, signalgrass (Brachiaria), cocklebur (Xanthium), Sesbania, Cassia, Alopecurus, oats (Avena), bluegrass (Poa), Matricaria, chickweed (Stellaria), bedstraw (Galium), and violet (Viola). Crops which were variously employed in these evaluations included cotton (*Gossypium hirsutum*), soybean (*Glycine max*), corn (*Zea maize*), milo (*Sorghum bicolor*), wheat (*Tritium aestivum*), sugarbeet (*Beta vulgaris*), rice (*Oryza sativa*), carrot (*Daucus carota*), and barley (*Hordeum vulgare*).

In summation, compounds submitted for further evaluation showed varying activity depending on the compound and the evaluation employed. Most compounds showed better activity in controlling grasses than broadleaf weeds, and most demonstrated better activity in pre-emergence than post-emergence application. Some compounds demonstratred good activity in nearly all types of application. Some compounds demonstrated good control in tests at application rates ranging as low as 0.06 pound per acre (0.065 kg/ha).

TABLE II
GREENHOUSE HERBICIDE TEST RESULTS

| Cmpd. No. | Application Rate (lb/A) | Method | FT | WG | WO | AMG | VL | MD | YNS |
|---|---|---|---|---|---|---|---|---|---|
| 1 | 4.00 | PES | 90 | 30 | 0 | 5 | 30 | 100 | 0 |
|  | 4.00 | POS | 0 | 20 | 0 | 10 | 80 | 85 | 0 |
| 2 | 4.00 | PES | 10 | 10 | 0 | 0 | 0 | 80 | 0 |
|  | 4.00 | POS | 0 | 0 | 0 | 10 | 80 | 80 | 0 |
| 3 | 4.00 | PES | 100 | 100 | 100 | 100 | 100 | 100 | 80 |
|  | 4.00 | POS | 90 | 80 | 80 | 80 | 80 | 80 | 80 |
| 4 | 4.00 | PES | 100 | 100 | 100 | 100 | 100 | 100 | 80 |
|  | 4.00 | POS | 100 | 95 | 90 | 100 | 100 | 100 | 80 |
| 5 | 4.00 | PES | 100 | 100 | 95 | 80 | 100 | 100 | 50 |
|  | 4.00 | POS | 100 | 80 | 80 | 60 | 80 | 100 | 80 |
| 6 | 4.00 | PES | 10 | 20 | 10 | 10 | 10 | 100 | 10 |
|  | 4.00 | POS | 10 | 10 | 10 | 20 | 40 | 100 | 10 |
| 7 | 4.00 | PES | 100 | 100 | 85 | 100 | 100 | 100 | 70 |
|  | 4.00 | POS | 90 | 85 | 90 | 60 | 80 | 100 | 80 |
| 8 | 4.00 | PES | 100 | 100 | 100 | 100 | 100 | 100 | 8 |
|  | 4.00 | POS | 80 | 80 | 80 | 80 | 80 | 80 | 80 |
| 9 | 4.00 | PES | 100 | 100 | 100 | 100 | 100 | 100 | 80 |
|  | 4.00 | POS | 80 | 80 | 80 | 80 | 80 | 80 | 80 |
| 10 | 4.00 | PES | 100 | 100 | 100 | 100 | 100 | 100 | 80 |
|  | 4.00 | POS | 100 | 95 | 100 | 80 | 80 | 100 | 80 |
| 11 | 4.00 | PES | 100 | 100 | 90 | 100 | 100 | 100 | 80 |
|  | 4.00 | POS | 100 | 90 | 100 | 80 | 80 | 80 | 80 |
| 12 | 4.00 | PES | 100 | 60 | 20 | 90 | 100 | 100 | 40 |
|  | 4.00 | POS | 50 | 50 | 50 | 20 | 50 | 50 | 0 |
| 13 | 4.00 | PES | 100 | 90 | 50 | 40 | 100 | 100 | 30 |
|  | 4.00 | POS | 100 | 80 | 80 | 80 | 80 | 100 | 80 |
| 14 | 4.00 | PES | 100 | 90 | 80 | 60 | 100 | 100 | 80 |
|  | 4.00 | POS | 90 | 80 | 80 | 80 | 80 | 100 | 80 |
| 15 | 4.00 | PES | 100 | 100 | 100 | 100 | 100 | 100 | 80 |
|  | 4.00 | POS | 100 | 80 | 100 | 100 | 100 | 100 | 80 |
| 16 | 4.00 | PES | 100 | 100 | 100 | 100 | 100 | 100 | 80 |
|  | 4.00 | POS | 100 | 90 | 90 | 100 | 85 | 100 | 80 |
| 17 | 4.00 | PES | 100 | 100 | 100 | 100 | 100 | 100 | 80 |
|  | 4.00 | POS | 100 | 80 | 80 | 60 | 80 | 100 | 80 |
| 18 | 4.00 | PES | 100 | 10 | 10 | 10 | 20 | 100 | 0 |
|  | 4.00 | POS | 20 | 20 | 0 | 10 | 70 | 100 | 0 |
| 19 | 4.00 | PES | 100 | 20 | 10 | 0 | 0 | 80 | 0 |
|  | 4.00 | POS | 0 | 0 | 0 | 0 | 0 | 0 | 0 |
| 20 | 4.00 | PES | 100 | 100 | 0 | 90 | 100 | 100 | 0 |
|  | 4.00 | POS | 100 | 50 | 0 | 60 | 30 | 80 | 0 |

Further Herbicidal Evaluation

Compounds showing good activity in the evaluations described above were submitted for one or more subsequent With respect to injury to crops, nearly all compounds tested produced unacceptable injury to sugarbeets even at relatively low levels of application. Some compounds showed good broad-spectrum activity but relatively low selectivity, causing injury to both weeds and crops in the same tests. Other compounds showed varying selectivity to certain crops, particularly wheat, rice and cotton, most notably with respect to rice in various methods of application.

In practice, a pure compound can be used as herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, tablets, powders and the like. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% compound; granules and pellets—1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | | | |
|---|---|---|---|
| Ingredient | Weight % | | |
| Oil | | | |
| Active Compound | 1 | | |
| Oil solvent-heavy aromatic naphtha | 99 | | |
| Total | 100 | | |
| Emulsifiable Concentrate | | | |
| Active Compound | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Active Compound | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |

-continued

| EXAMPLES OF TYPICAL COMPOSITIONS | | | |
|---|---|---|---|
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

What is claimed is:

1. A compound having the formula

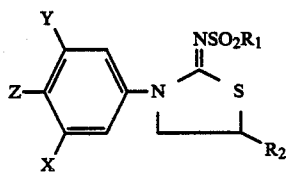

in which $R_1$ is $C_1$–$C_6$ alkyl; $C_1$–$C_6$ haloalkyl; $C_2$–$C_6$ alkenyl; mono- or di-($C_1$–$C_4$)alkylamino; phenyl; benzyl; or para-substituted phenyl or benzyl in which the substituent is halogen, cyano, nitro, $C_1$–$C_4$ alkyl, $C_1$–$C_4$ alkoxy, $C_1$–$C_4$ alkylthio or trifluoromethyl;

$R_2$ is hydrogen, methyl, ethyl or chloromethyl;

X is hydrogen, halogen, nitro, cyano, perhalomethyl, difluoromethyl, pentafluoroethyl, $C_1$–$C_4$ alkyl, $C_1$–$C_4$ alkoxy, trifluoromethylthio, difluoromethoxy, trifluoromethoxy, tetrafluoroethoxy, methylsulfonyl, trifluoromethylsulfonyl, phenoxy, pyridyloxy, halo-substituted-phenoxy or -pyridyloxy, trifluoromethyl-substituted-phenoxy or -pyridyloxy, $C_1$–$C_4$ alkyloximinomethyl, benzyloximinomethyl, 1-($C_1$–$C_4$ alkyl)oximinoethyl and 1-benzyloximinoethyl;

Y is hydrogen, halogen, nitro, cyano, perhalomethyl, difluoromethyl, pentafluoroethyl, $C_1$–$C_4$ alkyl, $C_1$–$C_4$ alkoxy, trifluoromethylthio, trifluoromethoxy, tetrafluoroethoxy, methylsulfonyl and trifluoromethylsulfonyl; and Z is hydrogen or fluoro if Y is hydrogen, or hydrogen if Y is other than hydrogen.

2. A compound according to claim 1 in which Y and Z are hydrogen.

3. A compound according to claim 1 in which X is halo, perhalomethyl, nitro, cyano, di- or trifluoromethoxy, difluoromethyl or tetrafluoroethoxy.

4. A compound according to claim 3 in which Y and Z are hydrogen.

5. A compound according to claim 3 in which Y is hydrogen and Z is fluoro.

6. A compound according to claim 1 in which $R_1$ is $C_1$–$C_6$ alkyl, $C_1$–$C_6$ haloalkyl, $C_2$–$C_6$ alkenyl, $C_1$–$C_4$ dialkylamino, or para-substituted phenyl in which the substituent is halo or $C_1$–$C_4$ alkyl.

7. A compound according to claim 6 in which Y and Z are hydrogen.

8. A compound according to claim 6 in which Y is hydrogen and Z is fluoro.

9. A compound according to claim 1 in which $R_1$ is $C_1$–$C_4$ alkyl, $C_1$–$C_4$ haloalkyl, $C_2$–$C_6$ alkenyl, $C_1$–$C_4$ dialkylamino, or para-substituted phenyl in which the substituent is halo or $C_1$–$C_4$ alkyl.

10. A compound according to claim 1 in which $R_2$ is ethyl.

11. A compound according to claim 10 in which X is trifluoromethyl, Y is hydrogen, Z is hydrogen and $R_1$ is methyl.

12. A compound according to claim 10 in which X is trifluoromethyl, Y is hydrogen, Z is hydrogen and $R_1$ is chloromethyl.

13. A compound according to claim 10 in which X is trifluoromethyl, Y is hydrogen, Z is hydrogen and $R_1$ is trifluoromethyl.

14. A compound according to claim 10 in which X is trifluoromethyl, Y is hydrogen, Z is hydrogen and $R_1$ is n-butyl.

15. A compound according to claim 10 in which X is chloro, Y is hydrogen, Z is fluoro and $R_1$ is chloromethyl.

16. A compound according to claim 10 in which X is cyano, Y is hydrogen, Z is hydrogen and $R_1$ is chloromethyl.

17. A compound according to claim 10 in which X is trifluoromethyl, Y is hydrogen, Z is fluoro and $R_1$ is chloromethyl.

18. A compound according to claim 10 in which X is chloro, Y is hydrogen, Z is hydrogen and $R_1$ is chloromethyl.

19. A compound according to claim 10 in which X is nitro, Y is hydrogen, Z is hydrogen and $R_1$ is chloromethyl.

20. A compound according to claim 10 in which X is trifluoromethyl, Y is hydrogen, Z is hydrogen and $R_1$ is dimethylamino.

21. A compound according to claim 10 in which X is trifluoromethyl, Y is hydrogen, Z is hydrogen and $R_1$ is ethyl.

22. A compound according to claim 10 in which X is trifluoromethyl, Y is hydrogen, Z is hydrogen and $R_1$ is n-propyl.

23. A compound according to claim 10 in which X is trifluoromethyl, Y is hydrogen, Z is hydrogen and $R_1$ is 3-chloropropyl.

24. A compound according to claim 1 in which $R_2$ is methyl, ethyl or chloromethyl.

25. A method for controlling undesirable vegetation comprising applying to said vegetation or the locus thereof a herbicidally effective amount of a compound according to claim 1.

26. A herbicidal composition comprising (a) a herbicidally effective amount of a compound according to claim 1 and (b) a herbicidally suitable diluent or carrier.

27. A method of controlling undesirable vegetation by applying a herbicidally effective amount of a composition according to claim 26.

* * * * *